(12) United States Patent
Amerling et al.

(10) Patent No.: US 9,794,409 B2
(45) Date of Patent: *Oct. 17, 2017

(54) ADAPTIVE SYSTEM WITH CALL CENTER AND TRUSTED NETWORK

(71) Applicant: GreatCall, Inc., San Diego, CA (US)

(72) Inventors: Aaron Amerling, La Mesa, CA (US); Scott Brenton, Vista, CA (US); Chris Gutierrez, San Marcos, CA (US); Kotaro Matsuo, Poway, CA (US)

(73) Assignee: GreatCall, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/194,311

(22) Filed: Jun. 27, 2016

(65) Prior Publication Data

US 2016/0309028 A1    Oct. 20, 2016

Related U.S. Application Data

(63) Continuation of application No. 14/803,681, filed on Jul. 20, 2015, now Pat. No. 9,380,153, which is a
(Continued)

(51) Int. Cl.
| | |
|---|---|
| *H04M 3/51* | (2006.01) |
| *H04M 3/38* | (2006.01) |
| *G06Q 10/10* | (2012.01) |
| *H04W 4/22* | (2009.01) |
| *G06F 19/00* | (2011.01) |
| *H04W 4/02* | (2009.01) |

(52) U.S. Cl.
CPC ........ *H04M 3/5183* (2013.01); *G06F 19/328* (2013.01); *G06Q 10/10* (2013.01); *H04M 3/38* (2013.01); *H04M 3/51* (2013.01); *H04M 3/5116* (2013.01); *H04M 3/5133* (2013.01); *H04W 4/22* (2013.01); *H04W 4/02* (2013.01)

(58) Field of Classification Search
CPC ........ H04M 3/38; H04M 3/51; H04M 3/5116; G06Q 10/10; G06F 19/328; G04W 4/22; G04W 4/02
USPC ...................... 379/37–45, 265.1, 265.09, 273
See application file for complete search history.

(56) References Cited

U.S. PATENT DOCUMENTS

| 5,805,670 A | 9/1998 | Pons et al. |
| 7,920,679 B1 | 4/2011 | Naim et al. |
| | (Continued) | |

*Primary Examiner* — Melur Ramakrishnaiah
(74) *Attorney, Agent, or Firm* — Kilpatrick Townsend & Stockton

(57) ABSTRACT

According to one aspect, a computer system comprises a processor, memory, and an interface to an electronic communication network. The memory holds instructions that when executed by the processor cause the computer system to maintain in electronic storage personal profiles of a number of clients of a service. At least one of the personal profiles includes identification of one or more entities authorized by the respective client to receive information about the client. The instructions further cause the system to produce a log associated with the client including information about the client. The information included in the log is filtered so that not all available information about the client is included in the log. The log is further made accessible via the electronic communication network to at least some of the one or more entities authorized by the client to receive information about the client.

15 Claims, 12 Drawing Sheets

Related U.S. Application Data continuation of application No. 14/486,843, filed on Sep. 15, 2014, now Pat. No. 9,088,653, which is a continuation-in-part of application No. 13/956,234, filed on Jul. 31, 2013, now Pat. No. 8,837,685, which is a continuation-in-part of application No. 13/617,564, filed on Sep. 14, 2012, now Pat. No. 8,515,020.

(56) References Cited

U.S. PATENT DOCUMENTS

| | | |
|---|---|---|
| 7,983,398 B2 | 7/2011 | Spiridellis |
| 8,489,066 B2 | 7/2013 | Imming et al. |
| 8,515,020 B1 | 8/2013 | Amerling et al. |
| 8,837,685 B2 | 9/2014 | Amerling et al. |
| 9,088,653 B2 | 7/2015 | Amerling et al. |
| 2003/0012344 A1 | 1/2003 | Agarwal et al. |
| 2004/0218732 A1 | 11/2004 | Menard et al. |
| 2006/0202819 A1* | 9/2006 | Adamczyk ........... G08B 25/005 340/539.18 |
| 2007/0023515 A1 | 2/2007 | Urken |
| 2007/0087726 A1 | 4/2007 | McGary et al. |
| 2007/0121799 A1 | 5/2007 | Binning |
| 2008/0166992 A1* | 7/2008 | Ricordi ................ A61B 5/0002 455/404.2 |
| 2008/0304630 A1 | 12/2008 | Nguyen et al. |
| 2009/0210241 A1* | 8/2009 | Calloway ............... G06Q 10/10 705/317 |
| 2009/0216859 A1 | 8/2009 | Dolling |
| 2010/0185460 A1* | 7/2010 | Nadler ................. G06F 19/322 705/3 |
| 2011/0151829 A1 | 6/2011 | Velusamy et al. |
| 2011/0192899 A1 | 8/2011 | Abdulhayoglu |
| 2011/0244872 A1 | 10/2011 | Quinn |
| 2012/0005285 A1 | 1/2012 | Lin |
| 2012/0129485 A1 | 5/2012 | Hebbar et al. |
| 2012/0191488 A1 | 7/2012 | Alperin |
| 2012/0208490 A1 | 8/2012 | Imming et al. |
| 2013/0305378 A1 | 11/2013 | Johnson et al. |

* cited by examiner

300

PERSONAL CLIENT PROFILE

<u>Client number</u>     555-555-555

<u>Client Information</u>
    Client Name:    Elizabeth Smith  (Betty)
    Address:    123 Main St.
        Smalltown, VA
    Age:  86

<u>Special Situations</u>
    Lives alone

<u>Contact Information</u>
    Barbara Jones (Daughter) 555-666-6666
    John Smith (Son)           555-777-7777

<u>Medical Conditions</u>
    Asthma
    Elevated blood pressure
    High cholesterol <u>Medications</u>
    Blood pressure
    Cholesterol medication <u>Medicine Allergies</u>
    Penicillin <u>Preferred Language</u>
    German <u>Trusted Network Contact Information</u>

| Name | Phone | Email | Client? | # Contacts |
|---|---|---|---|---|
| Barbara Jones | 555-666-6666 | bjones@x.com | Y | 11 |
| John Smith | 555-777-7777 | jsmith@y.com | Y | 4 |
| Tom Davis | 555-888-8888 | tdavis@z.com | N | 2 |
| Mary Lewis | 555-999-9999 | mlewis@w.com | Y | 3 |

PERSONAL CLIENT PROFILE

<u>Client number</u>    555-555-555

<u>Client Information</u>
    Client Name:    Elizabeth Smith  (Betty)
    Address:        123 Main St.
                  Smalltown, VA
    Age: 86

<u>Special Situations</u>
    Lives alone

<u>Contact Information</u>
    Barbara Jones (Daughter) 555-666-6666
    John Smith (Son)         555-777-7777

<u>Medical Conditions</u>
    Asthma
    Elevated blood pressure
    High cholesterol <u>Medications</u>
    Blood pressure
    Cholesterol medication <u>Medicine Allergies</u>
    Penicillin <u>Preferred Language</u>
    German                                                             1401

<u>Trusted Network Contact Information</u>

| Name | Phone | Email | Client? | # Contacts | Level |
|---|---|---|---|---|---|
| Barbara Jones | 555-666-6666 | bjones@x.com | Y | 11 | 962 |
| John Smith | 555-777-7777 | jsmith@y.com | Y | 4 | 731 |
| Tom Davis | 555-888-8888 | tdavis@z.com | N | 2 | 221 |
| Mary Lewis | 555-999-9999 | mlewis@w.com | Y | 3 | 111 |

FIG. 14

ADAPTIVE SYSTEM WITH CALL CENTER AND TRUSTED NETWORK

CROSS-REFERENCES TO RELATED APPLICATIONS

This application is a continuation of U.S. patent application Ser. No. 14/803,681 filed on Jul. 20, 2015, entitled "Adaptive System With Call Center And Trusted Network," which application is a continuation of U.S. patent application Ser. No. 14/486,843 filed on Sep. 15, 2014, entitled "Adaptive System With Call Center And Trusted Network," now U.S. Pat. No. 9,088,653, issued Jul. 21, 2015, which is a continuation-in-part of U.S. patent application Ser. No. 13/956,234 filed Jul. 31, 2013, entitled "Adaptive System with Call Center and Trusted Network", now U.S. Pat. No. 8,837,685, issued Sep. 16, 2014, which is a continuation-in-part of U.S. patent application Ser. No. 13/617,564, filed Sep. 14, 2012, entitled "Adaptive System with Call Center and Trusted Network", now U.S. Pat. No. 8,515,020, issued Aug. 20, 2013, the entire disclosures of which are hereby incorporated herein by reference for all purposes.

BACKGROUND OF THE INVENTION

Some private organizations offer telephone-based assistance services. For example, a client of such a service may call a private response center to obtain navigation assistance, concierge services, health advice, or the like. In some cases, a customer service representative at the private response center may speak with the client and recognize that the client has an emergency, and may connect the client with the proper authorities such as a "9-1-1" public safety answering point or an equivalent.

In other cases, the client may be disoriented, unable to speak, or otherwise unable to communicate the nature of his or her call. In situations like this, there is a need for the private response center to have other ways of gaining information about the client and his or her condition, so that appropriate action can be taken.

In some scenarios, certain clients may require other kinds of assistance with errands, personal business, and the like. There is a need for a mechanism for facilitating such assistance.

BRIEF SUMMARY OF THE INVENTION

According to one aspect, a computer system comprises a processor, memory, and an interface to an electronic communication network. The memory holds instructions that when executed by the processor cause the computer system to maintain in electronic storage personal profiles of a number of clients of a service. At least one of the personal profiles includes identification of one or more entities authorized by the respective client to receive information about the client. The instructions further cause the system to produce a log associated with the client including information about the client. The information included in the log is filtered so that not all available information about the client is included in the log. The log is further made accessible via the electronic communication network to at least some of the one or more entities authorized by the client to receive information about the client.

BRIEF DESCRIPTION OF THE DRAWINGS

FIG. 3 illustrates an example personal profile.

FIG. 14 is an example personal profile in which each of the members of a client's trusted network is assigned a trust level indicator.

DETAILED DESCRIPTION OF THE INVENTION

The ensuing description provides preferred example embodiment(s) only, and is not intended to limit the scope, applicability or configuration of the disclosure. Rather, the ensuing description of the preferred example embodiment(s) will provide those skilled in the art with an enabling description for implementing a preferred example embodiment. It is understood that various changes may be made in the function and arrangement of elements without departing from the spirit and scope as set forth in the appended claims.

Specific details are given in the following description to provide a thorough understanding of the embodiments. However, it will be understood by one of ordinary skill in the art that the embodiments may be practiced without these specific details. For example, systems, structures, and other components may be shown as components in block diagram form in order not to obscure the embodiments in unnecessary detail. In other instances, well-known processes, procedures and techniques may be shown without unnecessary detail in order to avoid obscuring the embodiments. Furthermore, embodiments may be implemented by manual techniques, automatic techniques, or any combination thereof.

Figure 1:
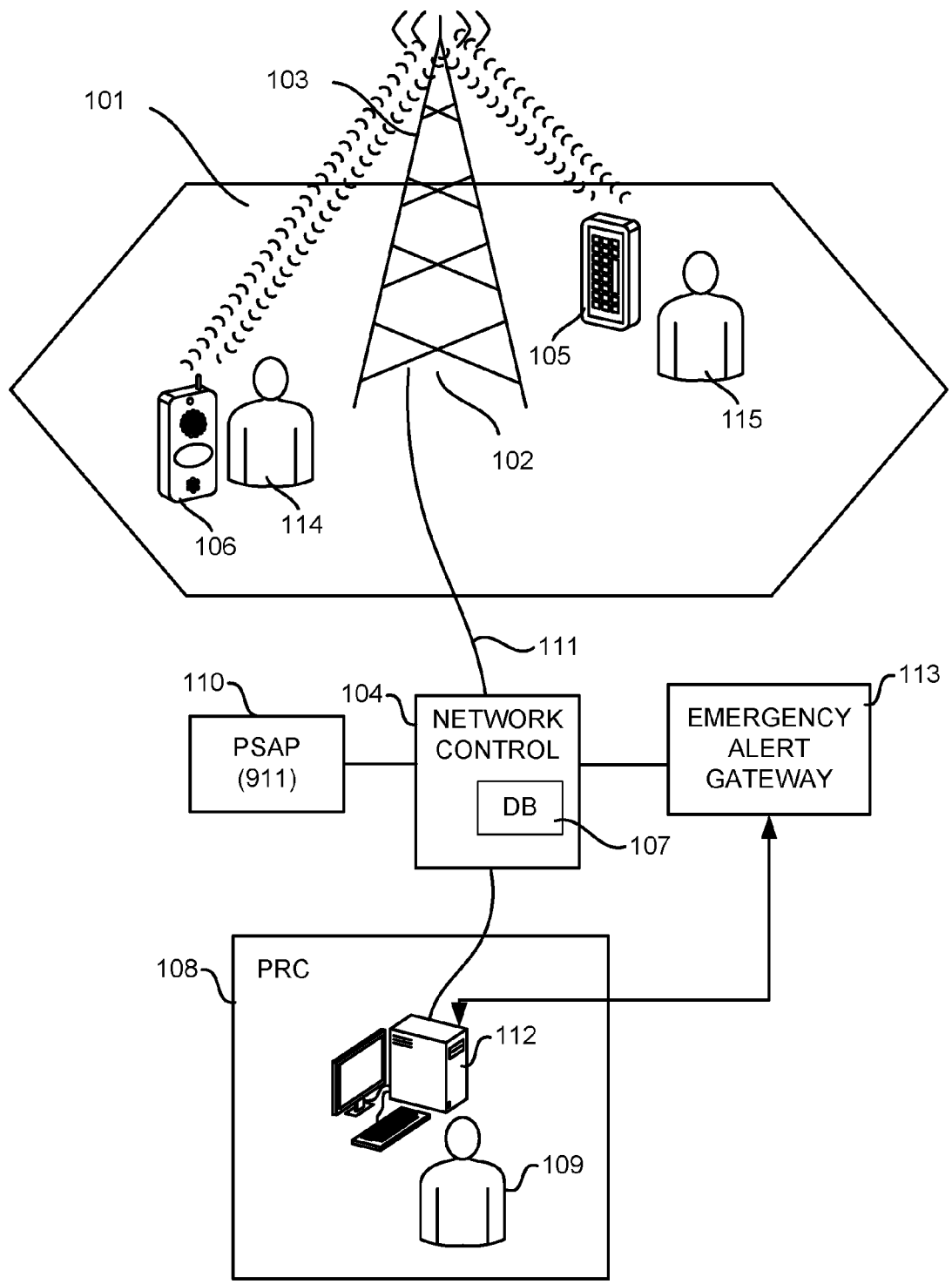
FIG. 1 illustrates a system in which the invention may be embodied.

FIG. 1 illustrates a system in which the invention may be embodied. Cell 101 is one cell of a cellular telephone network. Cellular networks are an especially efficient way to provide mobile telephone service. Each cell 101 is served by a respective base station 102, which may include an antenna mounted on a tower 103 or other structure. Each cellular telephone active in a particular cell can bi-directionally interact with the base station of the cell, enabling full duplex communication of data and/or voice. Each cell 101 is capable of communicating with mobile telephones within the respective cell according to a physical interface scheme (e.g., CDMA, LTE, GSM, GPRS, WiMax, etc.). Each base station 102 typically is capable of communicating simultaneously with several dozen or more different mobile telephones such as mobile telephone 105 or simplified communicator 106, which is described in more detail below.

Adjacent cells use different frequencies or coding to avoid interference. In this way, many mobile telephones can be supported using a limited spectra. The size and density of the cells 101 may be determined in part by the demand for service. While only one cell 101 is shown in FIG. 1, many other cells may be present, such that the cells collectively cover large contiguous areas. Special hand-off protocols may be used for maintaining communication with a particular telephone that moves from one cell to another during a call.

As shown in FIG. 1, each base station 102 communicates with a network controller 104. It will be understood that FIG. 1 is highly simplified, and network controller 104 represents a wide array of hardware, software, and other components performing a wide variety of functions. For example, network controller 104 may route calls between cells 101 and outside telephone providers, monitor telephone usage, maintain billing records for individual telephone accounts, perform diagnostic tests, and perform many other functions.

Network controller 104 may also include interfaces between the cellular network and other networks, organizations, or services.

Each active mobile telephone, such as mobile telephone 105, "registers" with a nearby base station, and network controller 104 keeps a database 107 listing which of the active mobile telephones is registered with which of the base stations. Network controller 104 uses database 107 to route incoming calls. For example, when a call is received at network controller 104 and intended to be routed to mobile telephone 105, network controller 104 consults database 107 to determine that mobile telephone 105 is registered with base station 102, and routes the incoming call accordingly.

The geographical locations of base stations 102 are fixed, and known to the operator of network controller 104. Thus, by virtue of database 107, network controller 104 "knows" at nearly all times the location of every active mobile telephone subscribed with the operator of network controller 104, at least to the accuracy of the size of cells 101. The size of each cell depends on the expected density of mobile telephones in a given area, on the topology of the surrounding landscape, and other factors, but typically cells range from a few hundred yards to several miles across. A particular geographical area may be served by more than one telephone service provider. Different telephone service providers may share network infrastructure, or may maintain separate controllers, base stations, towers, and other hardware. Each telephone service provider similarly "knows" the locations of all of its active subscribed mobile telephones.

While embodiments of the invention are described mainly in the context of cellular mobile communication, it will be recognized that the invention is not so limited, and embodiments may use fixed "landline" telephones, satellite telephones, voice-over-internet-protocol (VOIP) communications, or other kinds of communications devices.

A private response center (PRC) 108, is reachable via network controller 104, for example by dialing a particular telephone number. Private response center 108 may be operated, for example, by a response service provider who offers personalized assistance to clients who subscribe to the service. In some embodiments, the response service provider may offer personal health management advice, concierge services, navigational assistance, technical support for telephones used in conjunction with the service, or other kinds of personalized services deliverable by telephone. Private response center 108 may be staffed by customer service representatives 109 who answer inquiries from clients of the service. Such a service may especially appeal to clients with health or other impairments. For example, the service could include weekly or daily calls to the client for verification that the client is doing well, and if not, the customer service representative may offer to contact a family member, health care provider, or other resource that may be helpful to the client. The service could include these and other services sold as a package. Alternatively, PRC 108 may be a fully automated service designed to operate without human intervention.

Private response center 108 is not intended to be a substitute for a public safety answering point (PSAP) 110. A client of the service offered by private response center 108 would still be expected to dial 9-1-1 to reach PSAP 110 in the event of an emergency. However, while embodiments of the invention are described primarily in the context of a private response center, the invention is not so limited and may be embodied in a public facility such as PSAP 110. For example, as part of the Next Generation 9-1-1 initiative underway in the United States and Canada, it is expected that the capabilities and responsibilities of public safety answering points such as PSAP 110 will expand to include capabilities and components similar to those described herein for PRC 108. It is intended that the appended claims encompass both public and private facilities.

In one example scenario, the service provider that operates private response center 108 may also be a cellular telephone service provider, and may offer a private assistance service as an adjunct to cellular telephone service. The private response center 108 can be contacted for non-emergency service through a phone number, speed dial or other shortcut, for example by activating a 5 and * key combination on a telephone. The connection 111 between network controller 104 and private response center 108 is schematic. The actual connection could be by way of the Internet, a wireless connection, a voice-over-Internet-protocol (VOIP) connection, or a cellular telephone connection, or private response center 201 could be reached through a conventional wireline telephone system, or any other suitable connection method that enables a telephone user to reach private response center 108. Private response center 108 may be reachable via multiple methods.

PRC 108 includes a computer system 112 that may be used for various functions. For example, information about calls from clients may be displayed to customer service representative 109. Computer system 112 may store personal information gathered from clients that may be helpful in rendering assistance to the clients. Computer system 112 may assist customer service representative 109 in the performance of his or her job, for example automating telephone dialing and the like. While computer system 112 is illustrated as a single computer, it will be recognized that the term "computer system" encompasses many different kind of installations, including systems of multiple computers linked together. The multiple computers may be co-located or widely dispersed.

An emergency alert gateway 113 may enable law enforcement or other authorities to issue alerts to be broadcast via the cellular telephone system, for example to warn cellular telephone users of impending storms or other events that affect public safety. Such alerts may be issued via the Commercial Mobile Alert System (CMAS) currently being deployed in the United States, or via other systems. The CMAS system enables authorities to send text messages to active cellular devices in targeted geographic areas. These text messages may reach people that would otherwise not be notified by other means.

FIG. 1 also illustrates a client 114 of PRC 108, currently positioned in cell 101. Client 114 uses a simplified communications device 106, described in more detail below. Another cellular telephone user 115 uses fully-featured mobile telephone 105. User 115 may or may not be a client of PRC 108.

Figure 2:
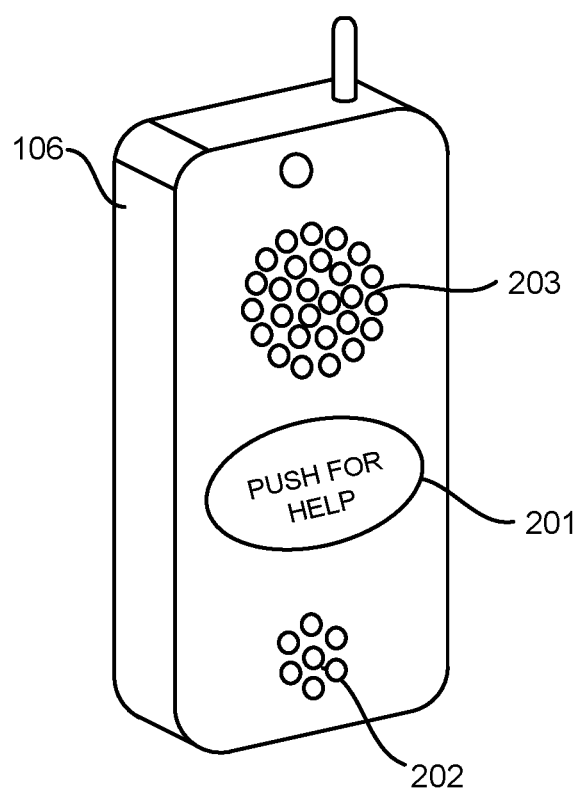
FIG. 2 illustrates a simplified communications device, in accordance with embodiments of the invention.

FIG. 2 illustrates simplified communications device 106 in more detail, in accordance with embodiments. Example communications device 106 may internally be a fully-featured cellular telephone, but has a simplified input interface comprising only one button 201. Communications device 106 may also be referred to as a "personal security device" or an "emergency communicator." A client of private response center 108 may wear communications device 106 on his or her person, and can use it to contact private response center 108 whenever assistance is needed. For example, communications device 106 may be configured to dial private response center 108 when button 201 is pressed. This greatly simplified input interface may be especially helpful to clients with impairments such as poor vision or coordination that make it difficult to operate a conventional cellular telephone that has many small keys. The single-button interface assures that private response center 108 will be called without the client having to press a sequence of keys. In the event of an emergency, private response center 108 may route the call to the proper authorities, if necessary. Communications device 106 further includes a microphone 202 and a speaker 203, enabling telephone or telephone-like communication.

In some embodiments, communications device 106 periodically reports its geographical location to PRC 108. Communications device 106 may determine its location using an internal global positioning system (GPS) receiver, by requesting that the cellular network estimate the location of communications device 106, or by any other suitable method or combination of methods. Systems and methods of monitoring the location of a communications device are described in more detail in U.S. patent application Ser. No. 13/026,158 filed Feb. 11, 2011 and titled "Systems and Methods for Determining Caller Locations", the entire disclosure of which is incorporated by reference herein for all purposes.

Referring again to FIG. 1, user 115 may also be a client of PRC 108, but rather than using a special-purpose communicator such as communications device 106, user (and client) 115 uses fully-featured cellular telephone 105, which may be a so-called "smart phone". A smart phone includes a processor and operating system such that it can be customized by installing application software selected by the user. In the example of FIG. 1, user 115 may have installed a special application that provides quick access to PRC 108, performs periodic location determinations and reports them to PRC 108, and the like. The application may also enable PRC 108 to contact user 115 in a secure manner, as is described in more detail below.

In embodiments where a device such as communications device 106 or cellular telephone 105 periodically determines and reports its location, the location determinations may be performed as accurately as possible, while minimizing network data traffic associated with some location determining methods. However, the location determinations may not provide information as detailed as might be desired. For example, communications device 106 or cellular telephone 105 may be indoors, and not able to obtain a position fix using a GPS receiver. Location determinations provided by the cellular telephone network may not be as precise as may be desired to locate a user of the device.

Preferably, PRC 108 collects profile information about each of its clients and stores the profile information, for example at computer system 112. When a client contacts PRC 108 for assistance, that client's profile may be retrieved and presented to the answering customer service representative 109, so that the customer service representative can better provide assistance. FIG. 3 illustrates an example personal profile 300, for example of client 114 of PRC 108.

Example personal profile 300 includes such information as the client's name and address, medical conditions, current medications, and other information. Also included is a listing of contact information for other entities in a trusted network designated by the client, for example upon enrollment of the client in the service provided by PRC 108. In this example, the entities in the trusted network are people, for example relatives, neighbors, or friends of the client. The trusted network could also include other kinds of entities, for example a nursing home or assisted living facility where the client resides, a school the client attends, a church office, or another kind of entity. Preferably, many clients of PRC 108 have identified trusted networks and have provided contact information for entities in their respective trusted networks.

Some or all of the entities in the trusted network may be automatically notified whenever the client contacts PRC 108 for assistance. Alternatively, a customer service representative may initiate a contact with one or more members of the trusted network when needed. The customer service representative may select which of the trusted network members to contact based on the nature of the reason for the client's call to PRC 108. For example, if the client calls with a medical issue, the customer service representative may notify the client's family (in addition to contacting official emergency services personnel, if appropriate). If the client calls to report that he or she has fallen, the customer service representative may also notify a trusted neighbor of the client, who may be nearby and able to render immediate assistance.

It will be recognized that in this disclosure, reference to contacting a particular person such as a member of a client's trusted network encompasses sending a message or other signals to a device registered to that person, for example that person's cellular telephone, personal digital assistant, tablet computer, or the like. Because many of the example devices discussed are mobile and typically carried by their users, it is convenient to think of sending a message to a person's device as contacting that person.

Figure 4:
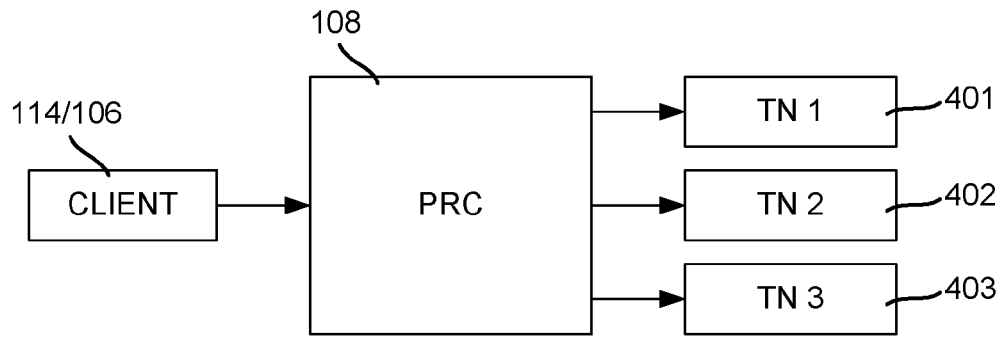
FIG. 4 illustrates a scenario in accordance with embodiments of the invention.

In a simple scenario illustrated in FIG. 4, client 114 has identified contact information for three trusted network members 401-403. Client 114 has contacted PRC 108, for example using communications device 106. PRC 108 notifies trusted network members 401-403 of the call from client 114. (Or more precisely, PRC 108 sends messages to the contact addresses of trusted network members 401-403, indicating that client 114 has contacted PRC 108.)

Figure 5:
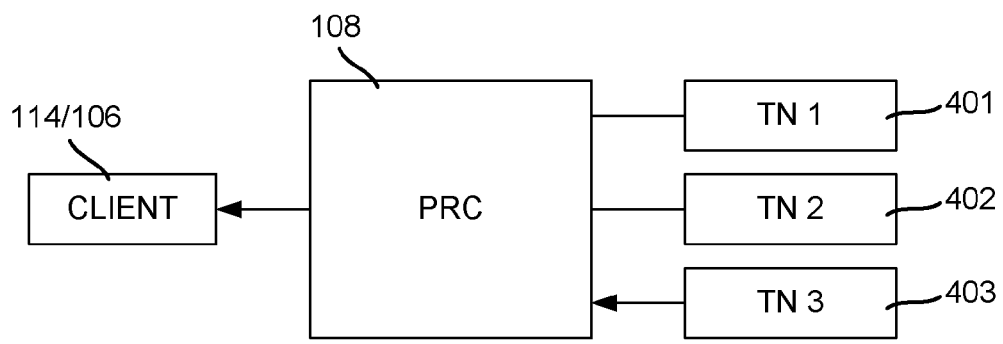
FIG. 5 illustrates another scenario in accordance with embodiments of the invention.

In some embodiments, members of the trusted network can contact PRC 108 on behalf of the client. For example, a neighbor or family member who has not been able to reach the client may request that PRC 108 try to contact the client via communications device 106. (While communications device 106 includes telephone capability, its telephone number may not be known to any entity other than PRC 108.) The trusted network member may simply call PRC 108 by dialing the telephone number of PRC 108, or may reach PRC 108 in other ways. For example, the trusted network member may use a smartphone with application software that can be used to call PRC 108, without the user needing to dial or even know the telephone number of PRC 108. In that scenario, the telephone number may be coded into the application software, and not visible to the user. PRC 108 may maintain a cross reference of entities in clients' trusted networks, so that when a call is received from a trusted network member who is not a client of PRC 108, the personal profile of the client whose trusted network the caller is in can be retrieved. This embodiment may be illustrated as in FIG. 5. One of the trusted network members 403 has initiated a call to PRC 108, which in turn has contacted client 114 (via communications device 106).

Figure 6:
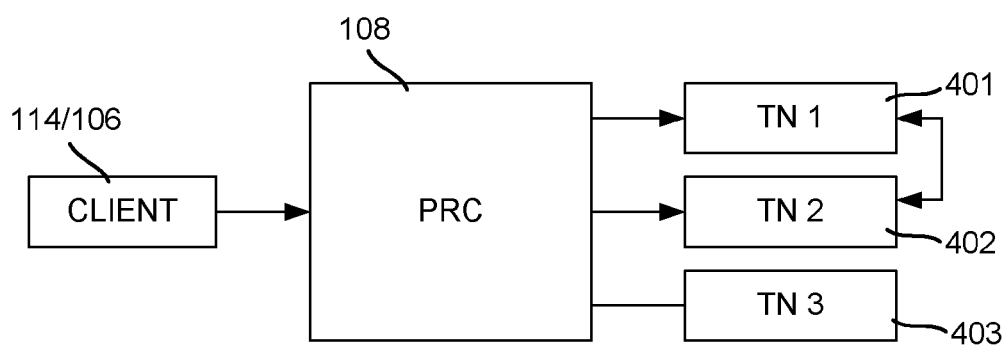
FIG. 6 illustrates another scenario in accordance with embodiments of the invention.

In other embodiments, PRC 108 may enlist the help of members of the trusted network in various interactive ways. One example is shown in FIG. 6. In this scenario, PRC 108 has been contacted regarding client 114. The original contact may have been initiated by client 114 or by a member of the client's trusted network, for example trusted network member 401. In handling the call, it may become apparent that another member of the trusted network, for example trusted network member 402 may be helpful. PRC 108 may arrange for trusted network members 401 and 402 to communicate directly with each other, for example via a conference call between PRC 108 and devices used by trusted network members 401 and 402, via a chat session conducted over the Internet, or by some other communication method.

Figure 7:
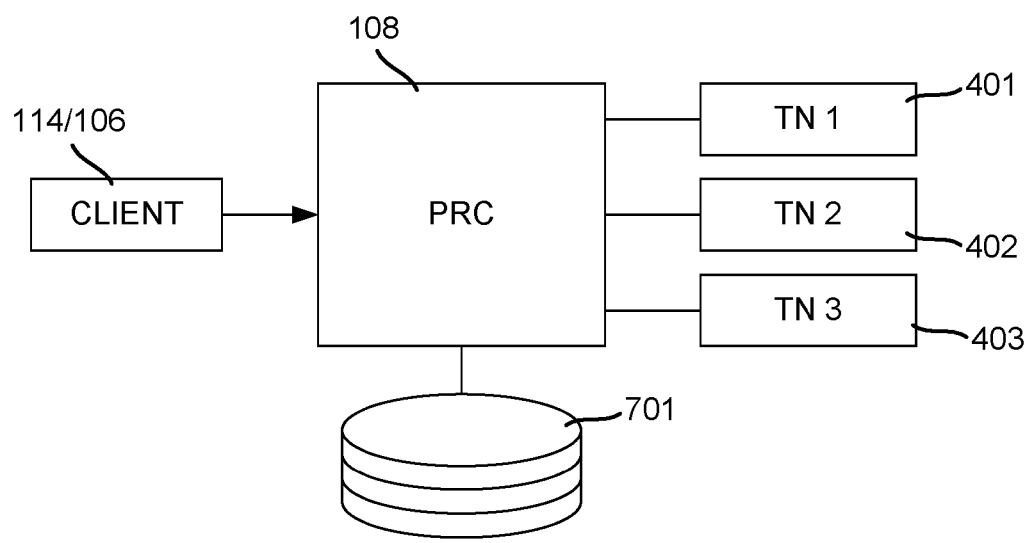
FIG. 7 illustrates another scenario in accordance with embodiments of the invention.

In other embodiments, for example as illustrated in FIG. 7, PRC 108 may maintain a database 701 of records of interactions between PRC 108 and client 114 and members of the clients trusted network. This information may be used in various ways. For example, as is shown in FIG. 3, one item of information that may be collected is a count of the number of times each trusted network member has been in contact with PRC 108 regarding client 114. This information may be presented in the client's personal profile shown to customer service representative 109 when client 114 calls PRC 108. Customer service representative 109 may use it to choose which trusted network member to contact first if it becomes apparent that a friend or family member may have information helpful in relation to the client's call. For example, customer service representative 109 may first try to contact the trusted network member having the most frequent interaction with PRC 108. Alternatively, computer system 112 may include algorithms that automatically select which trusted network member to contact based on predetermined or dynamic criteria such as proximity, frequency of interaction, relationship, schedule availability, social network status, the type of emergency or other incident that prompted the call to PRC 108, the skill levels of the trusted network members, or other criteria or combinations of criteria. To facilitate the automatic selection, customer service representative 109 may categorize the incoming call and supply the categorization to computer system 112. For example, customer service representative 109 may enter a particular code to indicate that a call relates to a client who is lost and needs directions, and a different code to indicate that a call relates to a client who is experiencing a medical emergency. Multiple codes may be entered for a single call, when the caller has multiple issues. Alternatively, computer system 112 may use a speech-to-text, speech recognition, or other algorithm to automatically detect key words spoken by the client, and automatically assign corresponding categorization codes for the call. In some embodiments, client 114 or trusted network members 401-403 may also have access to database 701, for example through a web page served over the Internet by computer system 112. In this way, trusted network members may be informed of real time interactions between PRC 108 and the client. In addition, trusted network members can also provide information to PRC 108 that is visible by all trusted network members. These kinds of interactions are described in more detail below.

In some embodiments, PRC 108 may automatically select which member or members of the trusted network to solicit for additional information or other help. For example, PRC 108 may select for solicitation the trusted network member identifiable as physically closest to the caller in the event of an incident that calls for immediate personal assistance to the caller, for example if the caller is lost, suffering a medical emergency, or the like. In other examples, the selection of whom to solicit for additional information may be based at least in part on one or more of relevant skills of trusted network members, frequency of contact between PRC 108 and a trusted network member, and the type of emergency or other incident that prompted the call to PRC 108. In some embodiments, the selection of whom to solicit for additional information may be based at least in part on who in the trusted network is used by or recommended by others, based on historical data, voting mechanisms, self-advertising, or the like.

In other embodiments, PRC 108 may automatically solicit additional information from the selected trusted network members or others. For example, the system may identify members of the trusted network who can help, and may contact them via text message, email, automated phone call, or other messaging or communication method. In another example, PRC 108 may automatically extract relevant information from another automated system such as a shared calendar, social media update, or other share source on the Internet. This information may provide additional data such as the location, activities, or motives of the client or other persons, the timeframe in which events may occur, or other details about the situation, environment, or the events surrounding the client.

In other embodiments, PRC 108 may prioritize members of the trusted network to contact, creating an ordered list. For example, PRC 108 may order the list of contacts based on proximity, such that the closest contact can be reached in the event of an incident that calls for immediate personal intervention, such as when the caller is lost or experiencing a medical emergency. In other examples, the prioritized list of whom to contact or solicit for additional information may be based on one or more of relevant skills of the trusted network members, frequency of contact of the trusted network members, the type of incident or emergency that prompted the call to PRC 108, proximity to the caller, and who in the trusted network is used or recommended by others, based on historical data, voting mechanisms, self-advertising.

In other embodiments, PRC 108 may automatically select members from the trusted network of another user to help for a particular type of emergency. For example, PRC 108 may identify a first responder who is close to the client needing help and who may be able to reach the client more quickly than official emergency services personnel. In another example, PRC 108 may identify a user that is trusted in many other people's networks, and who may be able to provide a particular service or information that is relevant to the emergency at hand. PRC 108 can identify this person using the prioritization mechanisms described above, or by a voting mechanism that helps identify those who are most likely to help. Other examples include ordering the list of all contacts in trusted networks based on proximity, such that the closest contact can be reached when proximity is important to address the incident that prompted the call to PRC 108, for example a client who is lost or is undergoing a medical emergency or the like. In other examples, the selection may be based on one or more of relevant skills, frequency of contact, type of incident, and who in the trusted network is used or recommended by others, based on historical data, voting mechanisms, self-advertising.

In yet another example, the trusted network may comprise non-person entities such as devices, systems, computer programs or other technologies that a call center has predetermined specific privileges to interact with as determined by their trust rank. In one example, a heart monitor may have the privilege to call PRC 108 on behalf of the client and provide data if the heart monitor recognizes irregular activity. In another example, a home automation system may contact PRC 108 with a key code to unlock the doors of the house. In yet another example, a medication management application can send a list of medications taken recently to PRC 108 if the client is incapacitated.

In another embodiment, PRC 108 may automatically solicit additional information from non-person entities such as devices, systems, computer programs or other technologies that a call center has predetermined specific privileges to interact with as determined by their trust rank. For example, during a fire, the system may solicit information from network enabled fire alarms, video cameras, or other remote sensors to correctly identify the safest route to exit a building. In another example, the system may solicit information from additional networked enabled fire alarms to verify the accuracy of a fire alarm that triggered an alert. This verification mechanism can allow the system to suppress false alerts before contacting authorities.

Figure 8:
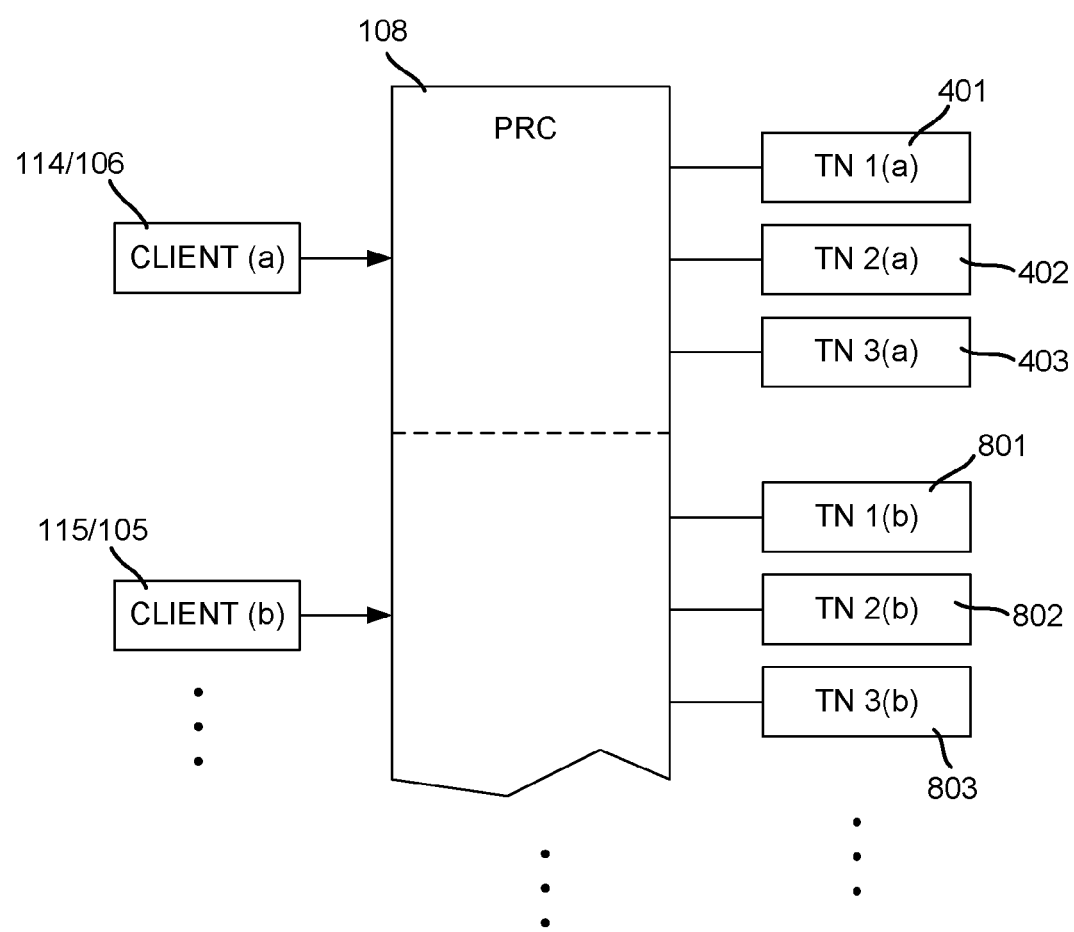
FIG. 8 illustrates that a response center may have multiple clients, each of which may have trusted networks, in accordance with embodiments of the invention.

Client 114 may be only one of many clients of PRC 108. FIG. 8 illustrates that PRC may have multiple clients, at least some of which may have trusted networks. In the example of FIG. 8, client 114 has identified contact information for three trusted network members 401-403 as previously described. In this example, user 115 is also a client of PRC 108, and has identified contact information for three trusted network members 801-803. In some embodiments, an entity may be included in the trusted networks of multiple clients.

Figure 9:
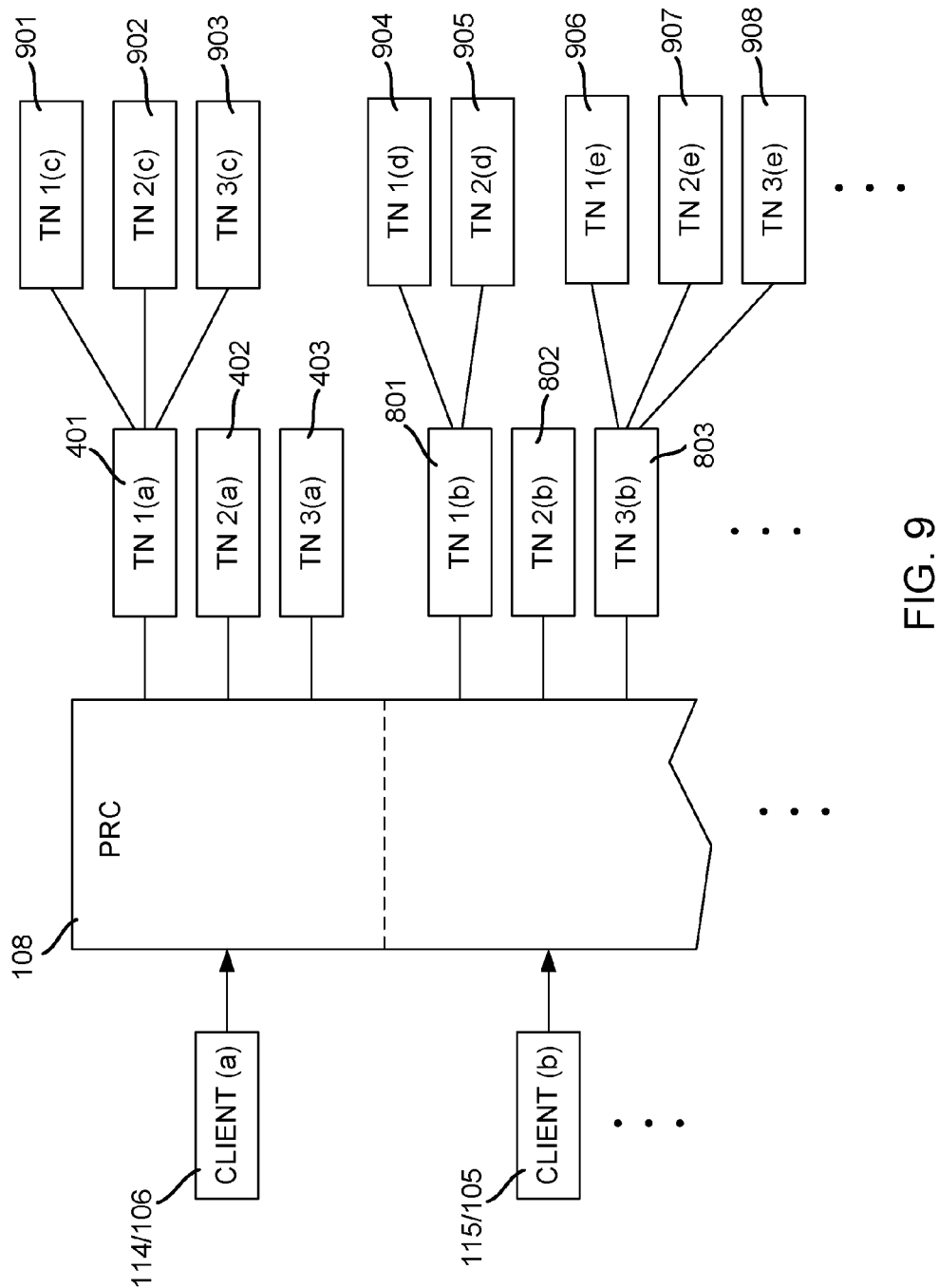
FIG. 9 illustrates a multi-level network, in accordance with embodiments of the invention.

In some embodiments, at least some members of clients' trusted networks may themselves be clients of PRC 108, and have identified contact information for entities in trusted networks of their own. This situation is illustrated in FIG. 9. In this example, trusted network member 401 (in the network of client 114) is also a client of PRC 108, and has identified contact information for trusted network members 901-903. Network members 901-903 may be referred to as second-level contacts in relation to client 114. Similarly PRC clients 801 and 803 (in the network of client 115) have identified contact information for network members 904-905 and 906-908 respectively. Although the network of trusted networks shown in FIG. 9 is shown as a simple hierarchy, many variations are possible. For example, clients may appear in each other's trusted networks. A single entity may be in the trusted networks of multiple clients, at the same or different levels. Many different interrelationships and interconnections are possible.

In addition, those entities in the extended network who are clients of PRC 108 may choose to make certain data and other information visible to PRC 108. For example, a client may make his or her electronic calendar visible to customer service representatives 109 at PRC 108. Clients could also provide access to their social networking sites, such as Facebook pages and the like. Other kinds of information to which a client could grant PRC 108 access include electronic calendars maintained by a spouse of the client or at the workplace of the client. Additionally, for at least some clients and trusted network entities, information may be publicly available about the clients or other related entities. For example, a friend or relative of a client may "tag" a digital photograph including the client and posted on the World Wide Web with the client's name.

This network of connections among clients and their trusted network entities, and the availability of information from other sources provide new opportunities for benefitting clients of PRC 108 and others.

In one example scenario, client 114 may call PRC 108 in need of assistance, but may not be able to supply his or her location. This situation could occur, for example, if client 114 becomes incapacitated after dialing PRC 108 or pressing button 201 on communications device 106, and if the most recent location information provided by communications device 106 to PRC 108 is untrustworthy for some reason, for example because the information is not recent. In this situation, PRC 108 may immediately try to contact the entities 401-403 identified by client 114 as being in his or her trusted network, using the contact information provided by client 114 upon enrollment or later. Entities 401-403 may be considered the most likely to know the location of client 114, so that help can be dispatched to the correct location.

Should PRC be unsuccessful in reaching any of entities 401-403 in a timely manner, PRC 108 may explore other information sources. For example, PRC 108 may attempt to contact second-level entities 901-903, in the trusted network of entity 401, on the assumption that these are the next most likely people or other entities to have information relating to client 114, or at least to trusted network member 401.

In addition or alternatively, PRC 108 may search secondary information sources. For the purposes of this disclosure, a secondary source is a source of information other than a direct contact with the client, a member of the client's trusted network, or a second- or higher-level contact in the client's extended network. For example, if client 114 has granted PRC 108 access to his or her electronic calendar or social networking pages, PRC 108 may search those sources for any indication of where client may be. For example, client 114 may have listed an appointment on his or her calendar corresponding to the time of the call received form client 114, or may have recently posted on a social networking page about an upcoming excursion that would encompass the time of the call. This posting may assist PRC 108 in locating client 114. In another example, public information sources may be searched. For example, a photo of client 114 may have been "tagged" recently on a social networking site with the name of client 114 and information about when and where the photo was taken. If the photo is recent enough, it may be suggestive that client 114 is still at or near the photo location.

This kind search may also be extended to trusted network entities and second-level network entities. For example, if a member of the client's trusted network has granted PRC 108 access to his or her electronic calendar, PRC 108 may search that entity's calendar for information that could relate to the client, for example a lunch appointment with client 114 encompassing the time of the call received by PRC 108 from client 114.

In another example, if an approximate location of client 114 can be determined, such as from a location determination received from the cellular telephone network, PRC 108 may search its records for other clients that are in the approximate vicinity, so that they might be able to provide information. The search may be prioritized by searching for members of the immediate trusted network of client 114, and then second-level connections (trusted network members identified by members of the client's trusted network).

Because clients may contact PRC 108 in the event of an emergency or other widespread event, PRC 108 may accumulate comprehensive and valuable information about the event. For example, several clients in the vicinity of a wildfire may call with questions about evacuation routes, fire suppression tips, and the like. In another example, clients affected by a power outage may call with questions about the effect of loss of refrigeration on medications.

In some embodiments, PRC 108 may act on this accumulated information for the benefit of its clients and others, preferably in ways that supplement but do not interfere with the efforts of official emergency response agencies. For example, by mapping the locations of callers, PRC 108 may be able to estimate the boundaries or direction of travel of a wildfire, and may provide that information to the official public safety or emergency management authorities. Examples of public safety and emergency management authorities include without limitation PSAP 110, local, state, or federal law enforcement agencies, fire departments, disease tracking and control agencies, weather monitoring agencies, a homeland security agency, civil defense services, and others. Callers may provide other information as well, for example which evacuation routes are congested and which are relatively free of traffic.

In some embodiments, PRC 108 may utilize its extended network of clients and designated contacts to proactively gather information. For example, in the wildfire scenario discussed above, PRC 108 could proactively contact clients or members of clients' networks seeking "on the ground" information about the extent and travel of the fire. If the map generated by PRC 108 includes gaps, contacts may be chosen to try to fill in those gaps. In some embodiments, PRC 108 may take responses received from members of clients' networks to update recommendations to clients in real time. For example, if PRC 108 discovers from clients or members of clients' networks that a particular evacuation route is available and uncongested, PRC 108 could then use that information to advise clients about the evacuation route.

In another scenario, a client may call PRC 108 (likely in addition to calling the authorities) for guidance about how to locate a missing child. Given the last known location of the child, PRC 108 could notify clients in the area, in the hope that one of them may see and report the child. This kind of notification could also be extended to clients' networks as well. In some embodiments, responses may be automated. For example, computer system 112 may actively search social media or photo sharing sites of clients or clients' networks to find recent pictures that have been tagged with the missing child's information, which could then be displayed for a client. In another example, a facial recognition search may be performed over social media sites or over real time data captured by security cameras that may be active in the vicinity of the child's last known location, enabling real time photo tagging of the missing child.

In some embodiments, the information gathered by the system can be used to predict how information, diseases or other person-to-person transferred entities spread. For example the Centers for Disease Control (CDC) may be trying to contain the spread of virulent disease and know that a client of PRC 108 has been infected. By looking at the trusted network of that client, and further to second level trusted networks, a likely path of infection may be found and used to determine who to contact that may likely have contracted the disease and who to proactively warn to take precautions against getting infected. Another example may be in the military defense field. For example, a client of the PRC 108 may have access to highly classified information and the Defense Department may wish to determine the risk if this information got out by analyzing the likely spread and reach of the client's trusted network as well as their second- and higher-level networks. Yet another example is in the advertising industry. Understanding the trust level inherent in the relationships between a client and his or her trusted network, the advertiser can choose to target a PRC client by advertising to their trusted networks. If a web marketing firm wants to determine if a person could be a "super influencer" and a good candidate to target in a campaign for a new medical product they can look at how many different trusted network members one person is in, and the reach of their 2nd level trusted networks and determine the maximum word-of-mouth spread potential and geo-location of an advertising message if the campaign was delivered to a particular trusted network member.

In some embodiments, PRC 108 may evaluate the severity, urgency, or extent of an event. For example, PRC 108 may consider the number of calls from clients relating to an event with the population density of areas from which the calls originated. An event such as an earthquake may affect a wide area, and may result in many calls, while a more localized event such as street flooding due to a water main break may result in fewer calls. PRC 108 may use its estimate of the severity, urgency, or extent of an event to determine whether proactive use of its network is justified, and to what extent.

In some embodiments, PRC 108 may use its extended network to distribute information for the benefit of its clients and others. For example, PRC 108 may learn of an approaching severe storm, and may wish to notify any clients residing in the expected path of the storm to take shelter. Preferably, any notifications are done in a manner that supplements and does not conflict with the efforts of government emergency management authorities. Clients may be notified by telephone call, electronic mail, text message, or other means. PRC 108 may choose the order of client notification so as to maximize the speed of information transfer. For example, clients who have large trusted networks may be notified first, if prioritization is necessary, on the assumption that they may pass the word to friends and loved ones. In another scenario, PRC 108 may choose the order of notification based on the size of clients' extended networks, that is, the number of second- or higher-level network entities in a client's network. In some embodiments, PRC 108 may provide information to official government authorities such as CMAS, the Integrated Public Alert and Warning System (IPAWS), or other systems.

In some embodiments, certain clients of PRC 108 may have skills or training particularly pertinent to emergency management. For example, clients of PRC 108 may include active or retired medical personnel, retired firefighters or law enforcement officers, and the like. Such clients may be flagged as having special skills, and information received from them may be considered especially reliable. In some embodiments, such clients may volunteer to be contacted proactively by PRC 108 in situations where their skills may be useful.

In some embodiments, PRC 108 may offer premium services to certain customers, who may or may not be clients of the other services offered by PRC 108. For example, businesses may have an interest in learning about events as they occur, and may subscribe to a notification service provided by PRC 108. PRC 108 would then compile reports and updates about events derived from the extended network of clients and client networks, and provide the reports and updates to subscribers. For example, PRC 108 may identify the extent of a power outage from calls received from clients, and may provide this information to a business customer such as an internet service provider or hospital who wishes to monitor the state of the power system.

Figure 10:
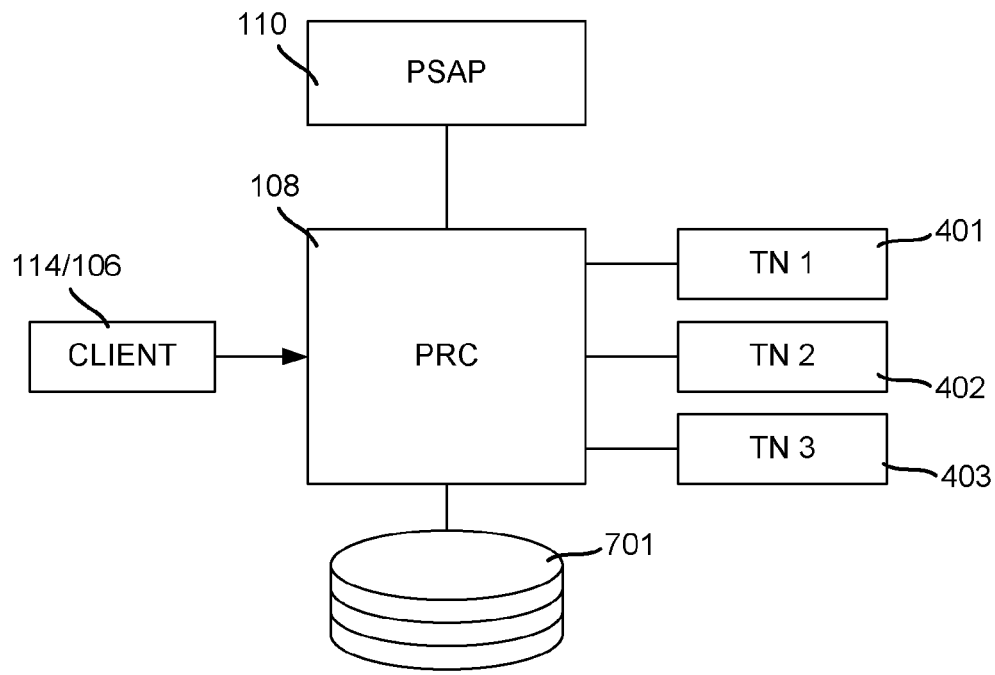
FIG. 10 illustrates an example scenario in accordance with embodiments of the invention.

FIG. 10 illustrates an example scenario, in accordance with embodiments of the invention. In FIG. 10, PRC 108 has been contacted regarding client 114. In this example, client 114 has called to report a serious fall, but is disoriented and cannot provide some needed information. A customer service representative 109 at PRC 108 may determine that this constitutes a medical emergency, and notifies PSAP 110 so that an ambulance can be dispatched. In addition, PRC 108 notifies trusted network entities 401-403. For example, one member of the client's trusted network could be a neighbor who may be able to lend comfort until the emergency services personnel arrive, and another member of the trusted network may be a relative who knows the client's medical history, how to enter the client's home, and other detailed information. PRC 108 may filter information shared with client 114 or trusted network entities 401-403. This filtering can be performed either through training of customer service representatives, or through automated methods, using logic and algorithms to identify use of certain words in certain contexts. For example, sensitive information, such as news of the death of a relative may be withheld from broadcast, and replaced with no notification, or a generic statement such as "Grandma was checked into St. John's Hospital. Call hospital for more information. 888-555-1111."

The notification of trusted network entities 401-403 may be by any suitable means, preferably as specified in the client's personal profile. For example, trusted network entities may be contacted by phone call, text message, electronic mail, or other methods. Some or all of trusted network entities 401-403 may carry smart phones or other communication devices capable of running application software, and may have installed a specialized application associated with PRC 108 as part of their service as members of the clients trusted network. In these cases, PRC 108 may send an electronic message to the smart phone to activate the application, which may then facilitate communication about the incident.

Figure 11:
FIG. 11 illustrates an example user interface screen in accordance with embodiments of the invention.

For example, a user interface such as user interface 1101 shown in FIG. 11 may be displayed on smartphones carried by each of trusted network entities 401-403. Preferably, only PRC 108 can activate the application to present user interface 1101, and thus a person seeing user interface 1101 can be assured that it describes an actual incident, and is not a ploy to gather information illicitly. Once one or more of trusted network entities 401-403 have indicated availability to help, they may be joined in a conference call, text-based chat, or a combination of media, so that they can collectively work to assist client 114. The parties can feel secure in sharing information as needed, because each is contacted and joined by PRC 108—a known and secure entity—and all of them have been designated by the client to participate in events like this example.

Figure 12:
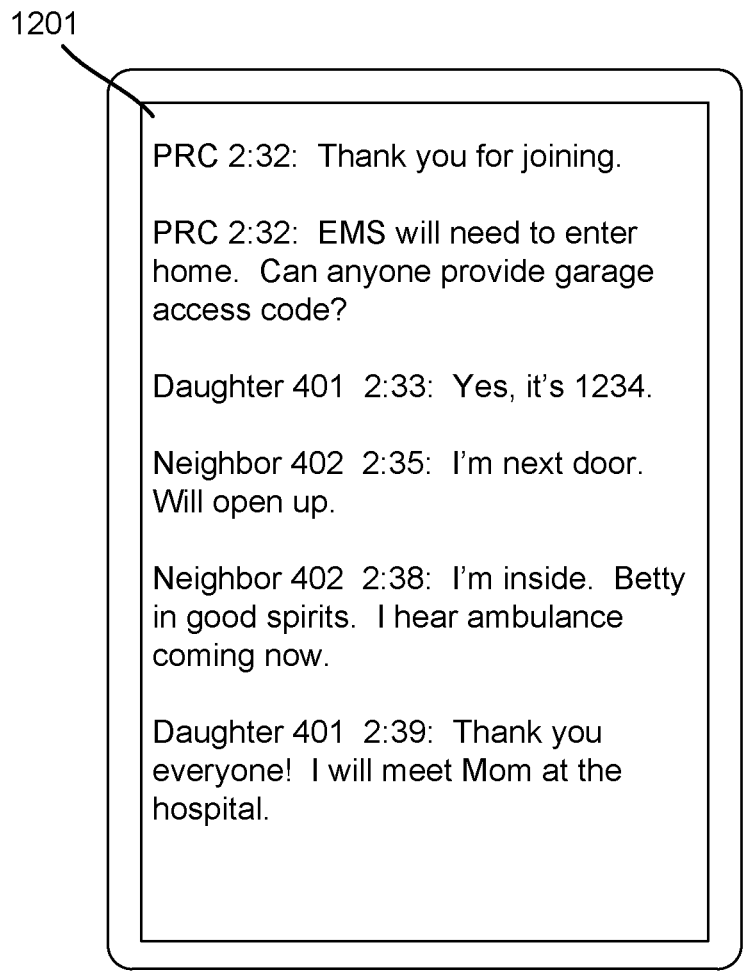
FIG. 12 illustrates another example user interface screen in accordance with embodiments of the invention.

FIG. 12 shows a second user interface screen 1201 that illustrates an example chat-type session conducted over the Internet in which PRC 108 and members of the trusted network arrange access for the approaching EMS personnel. In other embodiments a similar interaction may take place by conference call, or by a combination of methods. Other parties may be joined as well, for example emergency services personnel such as the dispatcher at PSAP 110. The system may automatically assign relationship tags to people in a trusted network, such as "Daughter" or "Neighbor", so that such people can be easily identified by other people in the chat-type session. This feature may be especially useful since people in the trusted network, even though may know that each person participating in the chat is trusted, may benefit from knowing the relationship of the trusted person to the client.

Preferably, a record of the communications among PRC 108, client 114, and trusted network members 401-403 is added to database 701, and becomes part of the account history of client 114. If the initial attempt to contact trusted network entities 401-403 is unsuccessful, PRC 108 may extend its search to second-level entities in relation to client 114, and attempt to contact network members such as members 901-908 if appropriate.

Figure 13:
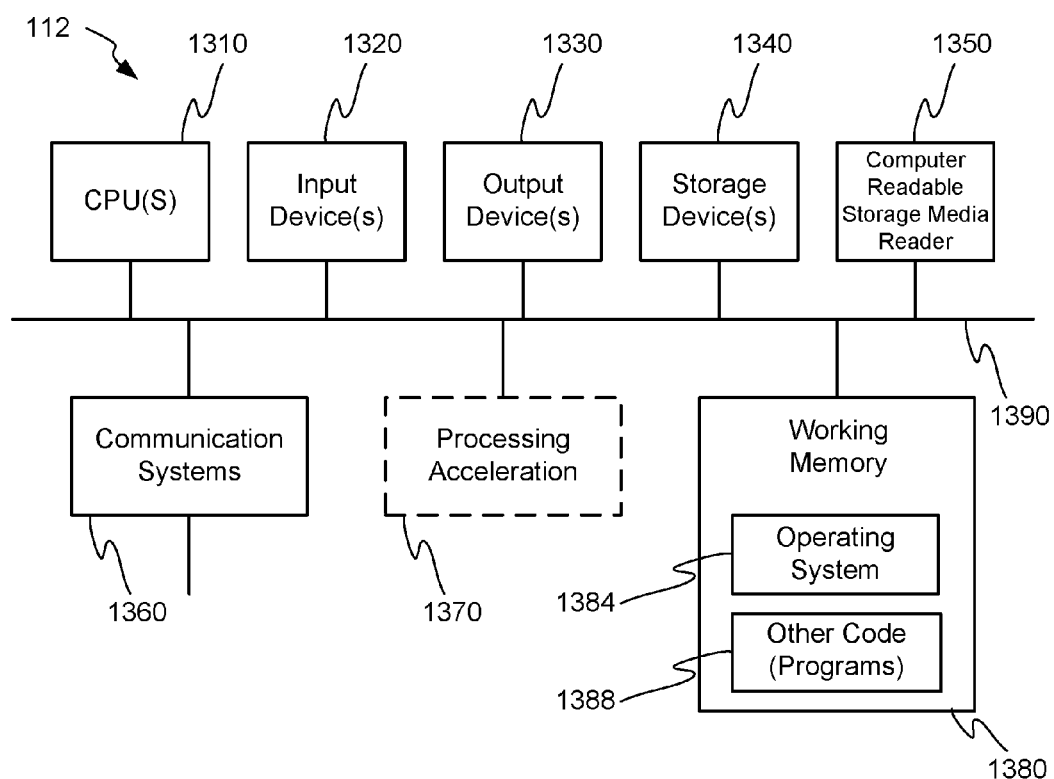
FIG. 13 illustrates a simplified block diagram of an exemplary embodiment of the internal structure of computer system.

FIG. 13 illustrates a simplified block diagram of an exemplary embodiment of the internal structure of computer system 112. The computer system 112 is shown comprising hardware elements that may be electrically coupled via a bus 1390. The hardware elements may include one or more central processing units 1310, one or more input devices 1320, and one or more output devices 1340. The computer system 112 may also include one or more storage device(s) 1340. By way of example, storage device(s) 1340 may be disk drives, optical storage devices, solid-state storage device such as a random access memory ("RAM") and/or a read-only memory ("ROM"), which can be programmable, flash-updateable and/or the like.

The computer system 112 may additionally include a computer-readable storage media reader 1350, a communications system 1360 (e.g., a modem, a network card (wireless or wired), an infra-red communication device, Bluetooth™ device, cellular communication device, etc.), and working memory 1380, which may include RAM and ROM devices as described above. In some embodiments, the computer system 112 may also include a processing acceleration unit 1370, which can include a digital signal processor, a special-purpose processor and/or the like.

The computer-readable storage media reader 1350 can further be connected to a computer-readable storage medium, together (and, optionally, in combination with storage device(s) 1340) comprehensively representing remote, local, fixed, and/or removable storage devices plus storage media for temporarily and/or more permanently containing computer-readable information. The communications system 1360 may permit data to be exchanged with a network, system, computer and/or other component described above.

The computer system 112 may also comprise software elements, shown as being currently located within a working memory 1380, including an operating system 1384 and/or other code 1388. It should be appreciated that alternate embodiments of a computer system 112 may have numerous variations from that described above. For example, customized hardware might also be used and/or particular elements might be implemented in hardware, software (including portable software, such as applets), or both. Furthermore, connection to other computing devices such as network input/output and data acquisition devices may also occur.

Software of computer system 112 may include code 1388 for implementing any or all of the function of the various elements of the architecture as described herein. For example, software, stored on and/or executed by a computer system such as system 112, can provide some of the functions of private response center 108 such as those discussed above. Methods implementable by software on some of these components have been discussed above in more detail.

While embodiments have been described above in the context of a private response center, it will be recognized that other embodiments may be implemented in a public safety answering point or other official entity.

The existence of the trusted networks of clients of PRC 108, and the maintenance of records of the trusted networks by PRC 108 enables additional capabilities of PRC 108, in accordance with additional embodiments. The repository of information held by PRC 108 may be considered a "trust store", and may be exploited in various ways.

In the embodiments described below, members of a trusted network of a client may be authorized by the client to take some action on behalf of the client. Such a relationship is more than a simple association, and more than a simple indication that a network member may be notified when the client has requested assistance from PRC 108. Rather, this relationship empowers the network member (preferably upon proper authentication) to act for the client, at least to some extent.

In some embodiments, a trust level or level of "trustedness" of a network member may be indicated for the network member. For example, FIG. 14 is an example personal profile in which members of the client's trusted network are assigned trust level indicators 1401. The trust level indicator may be a number, character string, word, textual description, or another kind of indicator that specifies what kinds of actions the network member can take on behalf of the client. In the example of FIG. 14, each trust level indicator 1401 is a multi-digit number, in which each digit specifies a level of authority for the network member in a particular category of action. Merely by way of example, the digits in the trust level indicators 1401 may be ascribed the following meanings.

TABLE 1

| Digit | Category | Example authorized acts at different levels |
|---|---|---|
| 1 | Medical | 0. Not authorized |
|   |   | 1. Administrative assistance, e.g. pick up prescription from pharmacy, schedule appointments, etc. |
|   |   | 2. Participate in routine heath care, e.g. make and attend doctor appointments, receive information re diagnosis and treatment |
|   |   | . . . |
|   |   | 9. Make end of life decisions |
| 2 | Personal business | 0. Not authorized |
|   |   | 1. Receive information only |
|   |   | 2. Authorize repairs and purchases up to $X |
|   |   | 3. Spend from designated account up to $Y monthly |
|   |   | 4. Unrestricted spending from designated account |
|   |   | 5. Conduct business, e.g. pay bills, start and stop utility service, etc. |
|   |   | 6. Make investment decisions |
|   |   | 7. Buy and sell real property |
|   |   | . . . |
| 3 | Security and Access | 0. Not authorized |
|   |   | 1. Access to client's home |
|   |   | 2. Access to client's computer |
|   |   | 3. Access to client's electronic mail accounts |
|   |   | . . . |

Any other suitable indication scheme may be used, having more or fewer categories, more or fewer levels of trustedness within a category, different methods of indicating the trust level, and other differences. However, using the example system in Table 1 above, the members of the trusted network shown in FIG. 14 have varying levels of authority to act on behalf of the client, as indicated by their trust levels 1401. In some embodiments, each trust level may be presumed to encompass all of the lower trust levels in a respective category. For example, a network member having a trust level of 5 in the personal business category would automatically be authorized to act for the client in the activities encompassed by trust levels 1-4 as well. In other embodiments, specific actions may be authorized or prohibited.

Some of the trust levels in Table 1 may require legal documentation. For example, for a member of the client's trusted network to have access to the client's medical records may require that the client execute an authorization form required by a medical provider, or required under law such as the Health Insurance Portability and Accountability Act (HIPAA) enacted in the United States. In another example, for a member of client's trusted network to be authorized to make investment decisions on behalf of the client may require that the client execute a power of attorney. Copies of any such written authorizations may be forwarded to and kept by PRC 108 as backup documentation for the trust levels maintained for the client.

With the trust levels and any appropriate authorizations in place, PRC 108 can act as a repository of authorization information for its clients, and may provide automated verifications of authorizations to facilitate assistance to the clients by members of the clients' trusted networks. For example, a member of the trusted network of client 114 (listed in FIG. 14) may offer to visit a local pharmacy and pick up a prescription medication for client 114, even though the network member may not be a family member of client 114, and may not be known to the pharmacy. The pharmacy may contact PRC 108 to verify that the network member is authorized to pick up the prescription.

In another example, trust may be granted to specific second-level entities such as entities 901-903 in trusted network 401-403. Someone who is determined to be highly trusted in the trusted network, for example, trusted entity 401, could use the trust store to pass along some measure of his or her trust between him or herself 401 and client 114. Specifically, trusted network entity 401 may have been designated by client 114 as having top-level medical trust privileges (end of life) for client 114, and has been requested to pick up client 114's medicine at the pharmacy. If for some reason trusted network entity 401 cannot pick up the medicine, he or she may pass client 114's lowest medical trust level designation to trusted network entity 401's top trusted network relation, 901 (i.e., his wife). In this way, second level entity 901 can pick up client 114's medicines for trusted network entity 401. Many variations may be envisioned. For example, in some embodiments, the level of trust that can be passed along may be limited only to the level possessed by the entity passing the trust. In other embodiments, entities may not be able to pass along their full levels of authority, may be limited in which other network members can be the recipients of trust, or may be subject to other limitations.

The steps performed by PRC 108 in embodiments of the invention may be performed at least in part using computer system 112 or a similar computer system. In some embodiments, some of the method may be performed with human assistance.

Figure 15:
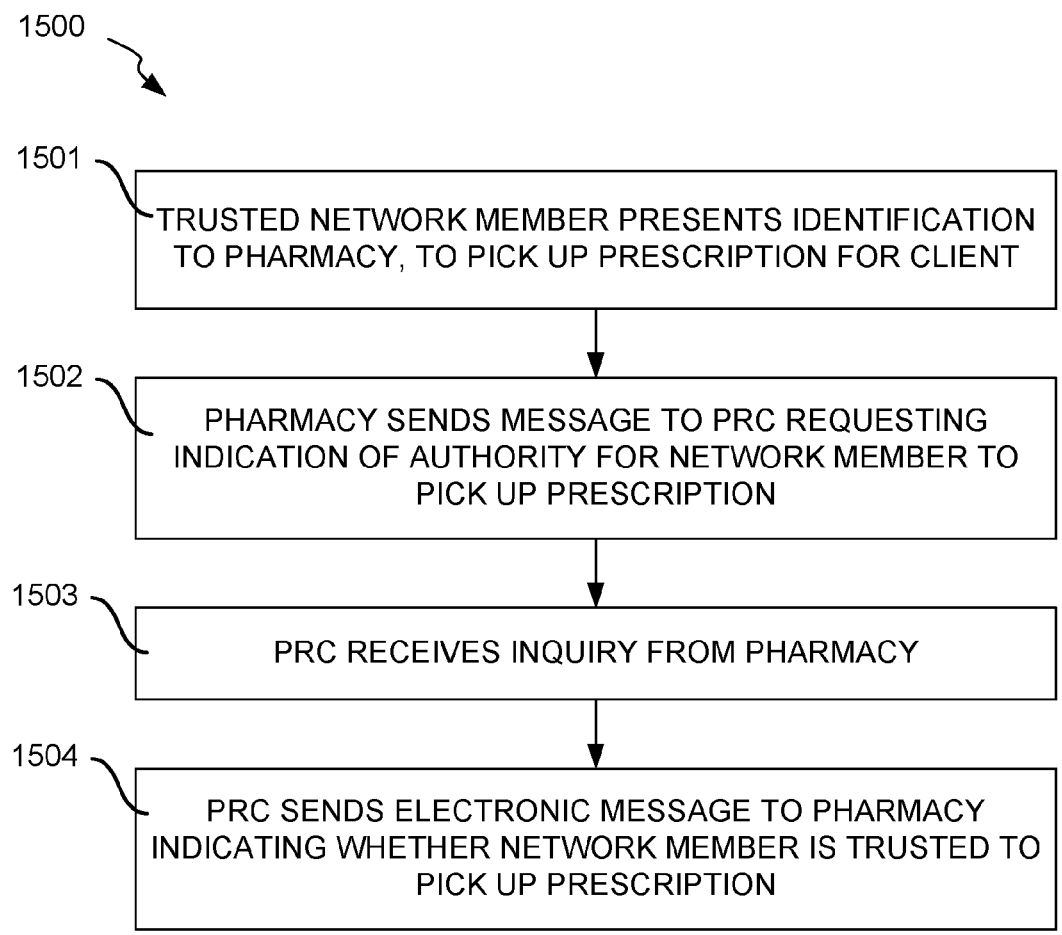
FIG. 15 illustrates a flowchart of a sequence of steps according to an embodiment.

FIG. 15 illustrates a flowchart 1500 of a sequence of steps according to an embodiment. In step 1501, the trusted network member presents identification to the pharmacy to pick up a prescription from the pharmacy on behalf of the client. In step 1502, the pharmacy sends a message to PRC 108, inquiring whether the network member is trusted by the client for whom the prescription is written. In step 1503, PRC 108 receives the inquiry from the pharmacy. In step 1504, PRC 108 sends an electronic message to the pharmacy, indicating whether the network member is trusted by the client to pick up the prescription.

Preferably, the pharmacy authenticates the identity of the network member, for example by requiring a photo identification or other means, and contacts PRC electronically to ask if the network member is authorized by the client. The pharmacy may also specify what kind of action the trusted network member is proposing to do on behalf of the client, in this example pick up a prescription medication. Upon receiving the request, PRC 108 can consult its database of profiles and verify that the network member does or does not have the authority to pick up the prescription. Preferably, the exchange between the pharmacy and PRC 108 is done electronically, for example through a voice phone call, an electronic mail exchange, an exchange of other kinds of electronic messages, or by other electronic methods. In some embodiments, the exchange may be automated, presuming proper programming of systems at both the pharmacy and PRC 108, so that no involvement of a customer service representative at PRC 108 is required.

In some embodiments, the return message from PRC 108 indicates only whether the trusted network member is or is not authorized to take the proposed action. That is, the message provides only a yes or no answer to the inquiry.

In other embodiments, the return message may include an indication of the trust level assigned to the particular network member by the client. The trust level may be understood to indicate one or more specific actions that the network member is authorized to take. For example, one of the trusted network members listed in FIG. 14 has a trust level of 731, indicating that this particular trusted network member is authorized to conduct small transactions on behalf of the client, limited to a particular dollar amount and using funds from only a specified account. This trust level may be taken to implicitly indicate that the network member is not authorized to take other actions requiring a higher trust level as indicated in Table 1, for example making investment decisions on behalf of the client. In some embodiments, PRC 108 may return only a trust level for the category of action the network member is taking on behalf of the client. In the example above, in which a trusted network member of client 114 is picking up a prescription medication, PRC 108 may return only the trust level for the network member in the "medical" category, so that the trust level in the "personal business" category and any other categories is not unnecessarily revealed.

In other embodiments, a trust level may explicitly disallow a network member from taking certain actions on behalf of the client. For example, the trust level indicator could be a binary string, each bit of which is a "1" or a "0" corresponding to a particular kind of action. The value of each bit (1 or 0) would indicate that the network member is or is not authorized to take the corresponding action on behalf of the client. Many other formats are possible, While the above example relates to a medical errand performed by a trusted network member on behalf of a client, other embodiments of the invention may relate to many other kinds of tasks. For example, a trusted network member may take a client's car to a repair shop for maintenance, and the repair shop may wish to verify that the trusted network member has the authority to incur the expense of the maintenance on behalf of the client. The repair shop contacts PRC 108 in a manner similar to that described in the pharmacy example above, and receives an indication of whether the network member is trusted to conduct personal business of this kind on behalf of the client. As before, the repair shop may require proper authentication of the trusted network member. The indication of whether the network member is authorized to conduct this kind of business may be in the form of a yes/no answer, or may include an indication of the level of trustedness of the network member.

According to another aspect, PRC 108 may search and analyze its store of trusted network information to identify particular individuals or other entities that are exceptionally well trusted. The degree of trust of a particular individual may be evaluated using any number of factors or combinations of factors.

For example, an individual who appears in the trusted network of more than one client may be considered to be especially trusted. This may be especially true of an individual appears in two or more otherwise-unrelated trusted networks. For example, when multiple family members are clients of PRC 108, the family members may be expected to appear in each other's trusted networks. However, an individual that appears in multiple trusted networks that do not share any other members may be considered to be especially trusted.

In another example, the trustedness of an individual or other entity may be evaluated based at least in part on the aggregate trust level assigned to that individual or other entity in the network or networks the individual or other entity appears in. Thus, an individual who has very high trust level indications in multiple trusted networks may be considered especially trusted. It will be recognized that the various possible indicators of trustedness may be combined. For example, an individual who has high trust level indications in multiple networks that otherwise unrelated may be considered exceptionally trusted.

In yet another example, the trustworthiness of an individual or other entity may be evaluated by blind authenticating information provided by another unrelated entity. Here, trustworthiness is different than trustedness. While trustedness may be evaluated based on evidence of how an entity is perceived, trustworthiness relates to the objective correctness and reliability of the entity. In some embodiments, a record is maintained by PRC 108 of the network members' history of information validity and accuracy. For example, a client is incapacitated and has two neighbors (Neighbor A and Neighbor B) in his or her trusted network, but the two neighbors have provided conflicting information about what medicine the client is taking. PRC 108 may look to the accuracy of information provided in the past by Neighbor A and Neighbor B, as validated against an unrelated third party. The third party may be, for example, another member of the trusted network who is unavailable at the time for a direct consultation. The third party could be a non-human entity, such as a medical monitor or other device that can provide direct objective information about the client. In another example, the third party may be a health professional. If Neighbor A has a history of proving accurate and validated information about the client, and Neighbor B has a history of providing inaccurate information, as validated by one or more third parties, then Neighbor A would be considered more trustworthy than Neighbor B. The unrelated third party would therefore act as a blind authentication means of the validity and accuracy of information provided by other members of the trusted network. In this way, some members of the trusted network can be used to judge other members of the trusted network. In addition, this function can be automated, creating a self-ranking trust network.

Once especially-trusted or trustworthy individuals or entities are identified, PRC 108 may use this information in a variety of ways. For example, at various times, PRC 108 may wish to send notifications to clients and members of clients' trusted networks. Situations in which such notifications may be used include broadcasting an alert about a missing child, or warning clients about an impending storm, fire, or other natural disaster. PRC 108 may choose to prioritize notifications so that the notifications are sent first to especially-trusted entities (which may include certain individuals), on the assumption that especially trusted entities will be more likely to disseminate the notification information promptly.

In another example, especially trusted or trustworthy entities may be surveyed to provide feedback or suggestions for better operation of PRC 108, on the theory that such entities may be the most reliable or will have the most experience interacting with PRC 108, and would therefore be most likely to have useful suggestions for PRC 108. In another example, PRC 108 may wish to recruit volunteers for a charitable project, and may approach identified especially trusted or trustworthy entities first. In another example, PRC 108 may recruit market research participants based on their trustedness or trustworthiness level with respect to a particular discipline. Many other uses of the trustedness or trustworthiness information gleaned from the records of PRC 108 may be envisioned. Preferably, any contacts with especially trusted or trustworthy entities are not intrusive and are respectful of the privacy of all persons involved.

In another example, trustedness or trustworthiness may be used as a weighted system for assigning a level of influence, for example in a voting system. The higher level an entity's trustedness, the more that entity's vote may counts in a democratic system. For example, after a death in the family the family members may make decisions about the disposition of the deceased's personal property, and the weight of each family member's vote can be determined by their level of trustedness as previously designated by the deceased.

In yet another example, the trusted network can act as a blind authentication system, in which a person in a trusted network can provide blind authentication of credentials about another member in their trusted network. For example, in the case that a client forgets his online banking password and his password recovery question answers, the bank can send some type of unique personal identifying information on the client to the client's trusted network. Examples of identifying information could include a photo taken from the client's phone or webcam, what schools the client attended, or a past address where the client lived. Members of the client's network can then verify the client's identity without knowing what the verification will be used for. Once the client's ID has been verified via his network, the client can then reset his or her password.

In another example, trusted network can be used as a means of transferring goods or money between two untrusted sources. Money or other goods can be transferred between overlapping trust networks by passing along an element of trust without actually transferring the physical goods, so that two untrusted sources can exchange goods, with the actual goods only being exchanged between two trusted sources. For example client A may want to provide $1000 to person C, who is not in client A's trusted network. Through the trust store, client A may give $1000 and an authentication phrase to a member of his trusted network. Client A can also separately give person C the same authentication phrase. Trusted network entity B then can give the $1000 and the authentication phrase to another party, person D, who is in both trusted networks of person B and person C. When person C provides person D with the authentication phrase person D gives the $1000 to person C.

According to another aspect, embodiments of the invention may be implemented outside the context of a private response center such as PRC 108. A trust store may be established by any entity, to provide individuals and organizations a mechanism for designating others as trusted to act on their behalf. The trust store itself may be offered as a service, and may be implemented at least in part using a specially-programmed computer system similar to computer system 112 discussed above.

While the principles of the disclosure have been described above in connection with specific apparatuses and methods, it is to be clearly understood that this description is made only by way of example and not as limitation on the scope of the disclosure. In addition, it is to be understood that all workable combinations of the features and elements disclosed herein are also considered to be disclosed.

What is claimed is:

1. A computer system, comprising:
 a processor;
 memory; and
 an interface to an electronic communication network;
 wherein the memory holds instructions that when executed by the processor cause the computer system to:
 maintain in electronic storage personal profiles of a number of clients of a service, wherein at least one of the personal profiles includes identification of one or more entities authorized by the respective client to receive information about the client, wherein at least some of the entities authorized by particular clients to receive information about the particular clients are members of trusted networks of the particular clients, the trusted network members having been previously authorized to act on behalf of the respective clients;
 produce a log associated with the client including information about the client, wherein the information included in the log is filtered so that not all available information about the client is included in the log; and
 make the log accessible via the electronic communication network to at least some of the one or more entities authorized by the client to receive information about the client.

2. The computer system of claim 1, wherein the log is also made available to the client, and the information included in the log is filtered before being made available to the client.

3. The computer system of claim 1, wherein the instructions further cause the computer system to:
 receive a contact related to a particular one of the number of clients; and
 include in the log information about the contact.

4. The computer system of claim 1, wherein the computer system automatically filters the information included in the log.

5. The computer system of claim 4, wherein the computer system automatically filters the information included in the log based on words included in the available information.

6. The computer system of claim 1, wherein the computer system filters the information included in the log with human assistance.

7. The computer system of claim 1, wherein at least some of the information is received from the client.

8. The computer system of claim 1, wherein at least some of the information is received from one of the entities authorized by the respective client to receive information about the client.

9. A method of operating a call center, the method comprising:

maintaining, by a computer system comprising a processor executing a program stored in a memory, in electronic storage personal profiles of a number of clients of a service provided by the call center, wherein at least one personal profile includes contact information for one or more entities designated by the client to receive information about the client, wherein one or more of the entities designated by clients to receive information about the clients are members of trusted networks of respective clients, the trusted network members having been previously authorized to act on behalf of the respective clients;

receiving a first piece of information related to a particular one of the number of clients;

producing a log associated with the particular client;

making the log accessible via an electronic communication network to at least some the one or more entities designated by the client to receive information about the client;

including the first piece of information in the log;

receiving a second piece of information related to the particular client; and filtering the second piece of information based on the content of the second piece of information so that the second piece of information does not appear in the log.

10. The method of claim 9, wherein filtering the second piece of information comprises automatically filtering the second piece of information using the computer system.

11. The method of claim 10, automatically filtering the second piece of information using the computer system comprises automatically filtering the second piece of information based on one or more words appearing in the second piece of information.

12. The method of claim 9, wherein filtering the second piece of information comprises filtering the second piece of information with human assistance.

13. The method of claim 9, further comprising receiving a contact related to the particular client, wherein either or both of the first and second pieces of information relate to the contact.

14. The method of claim 9, wherein at least one of the first and second pieces of information is received from the client.

15. The method of claim 9, wherein at least one of the first and second pieces of information is received from one of the entities designated by the client to receive information about the client.

\* \* \* \* \*